US008991722B2

(12) United States Patent
Friend et al.

(10) Patent No.: US 8,991,722 B2
(45) Date of Patent: Mar. 31, 2015

(54) MICROFLUIDIC APPARATUS FOR THE ATOMISATION OF A LIQUID

(75) Inventors: James Friend, Victoria (AU); Leslie Yeo, Victoria (AU); David Morton, Melbourne (AU); Michelle McIntosh, Warrandyte (AU); Aisha Qi, Clayton South (AU); Jenny Ho, Singapore (SG); Anushi Rajapaksa, Melbourne (AU)

(73) Assignee: Monash University, Clayton (AU)

( * ) Notice: Subject to any disclaimer, the term of this patent is extended or adjusted under 35 U.S.C. 154(b) by 294 days.

(21) Appl. No.: 13/318,976

(22) PCT Filed: May 11, 2010

(86) PCT No.: PCT/AU2010/000548
§ 371 (c)(1),
(2), (4) Date: Mar. 21, 2012

(87) PCT Pub. No.: WO2010/129994
PCT Pub. Date: Nov. 18, 2010

(65) Prior Publication Data
US 2012/0187209 A1  Jul. 26, 2012

(30) Foreign Application Priority Data
May 11, 2009  (AU) ............................... 2009902063

(51) Int. Cl.
*B05B 1/08*  (2006.01)
*A61M 11/00*  (2006.01)
(Continued)

(52) U.S. Cl.
CPC .......... *A61M 11/005* (2013.01); *A61M 15/0085* (2013.01); *A61M 2016/0021* (2013.01); *B05B 17/0607* (2013.01); *B05B 17/0661* (2013.01); *B05B 17/0684* (2013.01)

USPC ..... 239/102.2; 239/145; 239/326; 310/313 R; 310/313 B

(58) Field of Classification Search
CPC .......... A61M 11/005; A61M 15/0085; A61M 2016/0021; B05B 17/0607; B05B 17/0061; B05B 17/0653; B05B 17/0684
USPC .......................... 239/102.1, 145, 102.2, 326; 128/203.14, 203.15; 310/313 R, 313 B, 310/365, 366
See application file for complete search history.

(56) References Cited

U.S. PATENT DOCUMENTS

| 4,049,982 A | 9/1977 | Cohen |
| 4,301,093 A | 11/1981 | Eck |

(Continued)

FOREIGN PATENT DOCUMENTS

| DE | 19533297 | 3/1997 |
| EP | 0844027 | 5/1998 |

(Continued)

OTHER PUBLICATIONS

Chinese Patent Application No. 201080026065.3: Search Report dated Oct. 16, 2013, 8 pages.

(Continued)

*Primary Examiner* — Jason Boeckmann
(74) *Attorney, Agent, or Firm* — Baker & Hostetler LLP

(57) ABSTRACT

An apparatus (1) for the atomisation of a liquid including: a piezoelectric substrate (5) having at least one working surface (7), at least one electrode (9) supported on the piezoelectric substrate (5), a signal generating means (21) for applying an ultrasonic signal to said electrode (9) for generating a surface acoustic wave (SAW) in the working surface (7) of the piezoelectric substrate (5); a liquid delivery arrangement (11) including a wick (17) in contact with the working surface (7) for delivering liquid thereof, wherein liquid delivered to the working surface (7) is atomised by SAW irradiation.

7 Claims, 1 Drawing Sheet

(51) Int. Cl.
*A61M 15/00* (2006.01)
*B05B 17/06* (2006.01)
*A61M 16/00* (2006.01)

(56) References Cited

U.S. PATENT DOCUMENTS

| | | | |
|---|---|---|---|
| 5,831,492 A * | 11/1998 | Solie | 333/193 |
| 6,325,475 B1 | 12/2001 | Hayes et al. | |
| 6,407,650 B1 | 6/2002 | MacFarlane | |
| 7,891,580 B2 * | 2/2011 | Valpey et al. | 239/102.2 |
| 2002/0079987 A1 | 6/2002 | Yip et al. | |
| 2003/0173867 A1 * | 9/2003 | Mauchamp et al. | 310/311 |
| 2006/0065755 A1 * | 3/2006 | Sugita et al. | 239/1 |
| 2006/0180143 A1 * | 8/2006 | Lind et al. | 128/200.14 |
| 2006/0243820 A1 * | 11/2006 | Ng | 239/102.1 |
| 2008/0084134 A1 * | 4/2008 | Morita et al. | 310/313 A |

FOREIGN PATENT DOCUMENTS

| | | |
|---|---|---|
| EP | 1952896 | 8/2008 |
| JP | 58/32618 | 2/1983 |
| JP | 08/511966 | 12/1996 |
| JP | 2000/233158 | 8/2000 |
| JP | 2001/502666 | 2/2001 |
| JP | 2004/266632 | 9/2004 |
| JP | 2008/036406 | 2/2008 |
| JP | 2008073570 | 4/2008 |
| JP | 2008104966 * | 5/2008 ............ A61M 11/00 |
| JP | 2008104974 | 5/2008 |
| JP | 2008/544834 | 12/2008 |
| WO | WO 95/01137 | 1/1995 |
| WO | WO 98/10796 | 3/1998 |
| WO | WO 2006/086655 | 8/2006 |
| WO | WO 2007/135409 | 11/2007 |
| WO | WO 2010/129994 | 11/2010 |

OTHER PUBLICATIONS

European Patent Application No. EP 10774423: Supplementary European Search Report dated Oct. 30, 2013, 4 pages.
Guanglun et al., "A Low Loss SAW Filter Employing Single-Phase Unidirectional Transducer", Piezoelectrics & Acoustooptics, Feb. 20, 1994, 16(1), 1-6.
Japanese Patent Application No. 2012-510069: Office Action dated Mar. 14, 2014, 7 pages.

* cited by examiner

MICROFLUIDIC APPARATUS FOR THE ATOMISATION OF A LIQUID

CROSS-REFERENCE TO RELATED APPLICATIONS

This application is the National Stage of International Application No. PCT/AU2010/000548, filed May 11, 2010, which claims the benefit of Australian Application No. 2009902063, filed May 11, 2009, the disclosures of which are incorporated herein by reference in their entireties.

TECHNICAL FIELD

The present invention is directed to a microfluidic apparatus for the atomisation of a liquid. While the invention is described with respect to its use as a pulmonary delivery apparatus, it is to be appreciated that the invention is not restricted to this application, and that other applications are also envisaged.

BACKGROUND TO THE INVENTION

Gene therapy represents a new paradigm of therapy for diseases, where the disease is treated at the molecular level by restoring defective biological functions or reconstituting homeostatic mechanisms within cells. Effective gene therapy requires that the Deoxyribonucleic acid (DNA) successfully accesses the target cell, is taken up for internalisation into the cell, is trafficked through the cell after escaping the degradative pathway to the nucleus, to subsequently be transcribed and translated to produce a desired gene product.

The lung is an important target for gene delivery because aerosol delivery is a non-invasive technique and can directly target the vast surface area of the lung. Plasmid DNA (pDNA) can be introduced into the lung by aerosol inhalation. However, delivery efficiency and durability of the gene vectors to comply with stringent requirements are critical areas for this approach to be successful. Potential obstacles for current pulmonary delivery devices include the retention of the supercoiled structure of the plasmid in the aerosols to retain its transfecting ability and to comply with regulatory requirements on product quality, and to produce aerosol particles with appropriate sizes for optimal delivery to lung surfaces.

Numerous studies have been undertaken in order to determine the feasibility of pulmonary delivery devices in delivering non-complexed pDNA to the lungs. Unfortunately, the supercoiled tertiary structures of pDNA with sizes larger than 5 kilo-base pairs (kbp) have been found to be severely sheared into open circular and fragmented DNA by hydrodynamic shear and shock waves during nebulization in jet and ultrasonic nebulizers. The emergence of new devices such as mesh nebulizers, electrohydrodynamic (EHD) devices and miniaturized nebulization catheter devices have been said to offer greater aerosolization efficiency, and preserve the integrity of pDNA in the aerosols. However, these devices require more clinical studies to demonstrate this.

Inhalation therapy has become the treatment of choice for asthma and chronic obstructive pulmonary disease (COPD). Unlike oral dosing, inhalation therapy allows a high concentration of a drug to be administered and targeted directly to local inflammation sites within the lung, thereby enabling lower total dosages, reduction in systemic side effects, and potentially hastening the onset of action of the drug. Metered Dose Inhalers (MDIs) and Dry Powder Inhalers (DPIs) are commonly used for bronchodilator administration for asthma and COPD therapy; the patient inhales a pre-metered dose in a single forced inspiratory manoeuvre. There is a lively debate among researchers, however, in deciding whether MDIs or DPIs are the most effective or if continuous nebulization to a patient undergoing repeated tidal breathing for a period up to several minutes is required. Though the debate continues, critical factors in making such decisions are generally based on clinical judgements, taking into consideration such factors as dose level, drug efficacy and safety profile, patient age group, disease severity, ease of administration, and cost.

Nebulizers are capable of delivering more drug than current MDIs and DPIs because they operate over a longer period. Moreover, nebulizers do not require coordination skills from the patient, unlike MDIs, and do not require patient actuation via inhalation, unlike DPIs. Nebulizers are commonly used in acute cases of COPD or severe asthma attacks where the patient is unable to self-medicate. For this same reason, nebulizers may be more appropriate for paediatric and geriatric patient populations.

Historically, nebulizers have been large, cumbersome, less portable and more expensive than MDIs or DPIs. Furthermore, conventional nebulizers generally have low dose efficiencies; although more drug may be delivered into an aerosol, much of the aerosolized drug is subsequently wasted because:

1. aerosols are generated continuously, wasting drug as the patient exhales against the nebulizer's output,
2. the aerosols have polydisperse size distributions, with a significant fraction of droplets too large for deep lung deposition, and since
3. nebulizers typically have a large internal residual volume.

For inhalation therapy to be most effective, the droplet's aerodynamic behaviour (governed by Stokes' law) is of fundamental importance. For deep lung deposition, an aerodynamic diameter less than 5 μm or preferably 3 μm is considered appropriate, such that the aerosol can avoid inertial impaction in the oropharyngeal region. For deposition higher up in the airways, a larger aerodynamic diameter may be preferred. As a result, the aerosol droplet size is crucial to the efficacy of inhalation therapy, and therefore an ideal device capable of efficiently delivering high doses of a drug would permit precise control of the droplet size distribution and preferably offer large atomisation rates to deliver the desired dosage in as short a time period as possible to minimize patient distress and inconvenience.

Nebulization technology has rapidly progressed in recent years, with new methods that utilize ultrasound and electrohydrodynamic atomisation, allowing greater control over the atomisation process to provide aerosols with reduced spreads of polydispersity and with droplet size tuning capability. Furthermore, these methods may be miniaturized, offering an attractive alternative to the large and cumbersome nebulizers that are currently available commercially. Unfortunately, these methods have inherent limitations. For example, electrohydrodynamic atomisation is restricted to high voltage operation—typically several kilovolts—raising safety and reliability issues in consumer use. Various types of ultrasonic atomisation have been devised over the years, and the most common systems use a bath of liquid from which a piezoelectric disc generates an aerosol plume. These ultrasonic nebulizers are also relatively large in size, have limitations on output and size control, and often precipitate the solubilized drug onto the atomisation reservoir walls due to solvent evaporation, wasting the drug and requiring regular cleaning by the user. More recent designs using meshes for nebulization offer better portability, dosage rates, and aerosol monodispersity. The mesh has chemically or laser-cut microscopic holes, forming thousands of orifices that generate droplets under irradiation by ultrasound, although these meshes are prone to clogging, which significantly reduces throughput. In the context of these past and current technologies, a small, portable, reliable, and relatively cost-effective device remains out of reach, especially one that can effectively generate non-agglomerating droplet size distributions which are suitably monodisperse and less than 5-10 µm in diameter.

SUMMARY OF THE INVENTION

With this in mind, the present invention provides an apparatus for the atomisation of a liquid including:

a piezoelectric substrate having at least one working surface;

at least one electrode supported on the piezoelectric substrate;

a signal generating means for applying an ultrasonic signal to said electrode for generating a surface acoustic wave (SAW) in the working surface of the piezoelectric substrate;

a liquid delivery arrangement including a wick in contact with the working surface for delivering liquid thereof, wherein liquid delivered to the working surface by the wick is atomised by SAW irradiation.

The electrode may be in the form of an interdigital electrode. More preferably, the electrode configuration may be an elliptical, electrode width controlled single phase unidirectional transducer (EWC-SPUDT).

The electrode is preferably configured as EWC-SPUDT as this configuration gives the largest surface acoustic wave intensity into the liquid sitting on the substrate compared to straight standard and SPUDT-style interdigital transducer electrodes, circular EWC-SPUDTs, and other configurations known currently. For a given input power, the elliptical EWC-SPUDT therefore offers the best atomisation performance of these various configurations, and the width and ellipticity of the EWC-SPUDT so chosen is preferably tailored to the size of the liquid drop sitting upon the substrate. The relationship between the size of the droplet and the exit aperture (width) of the EWC-SPUDT depends on the liquid properties, but the ratio of drop diameter to exit aperture is preferably between 0.5 and 2.

Preferably more than one EWC-SPUDT may be used. For example, two may be used on very anisotropic piezoelectric materials like lithium niobate (class [3m]), while more can be used on less anisotropic materials like ZnO, AlN, or PZT.

The frequency of atomisation is preferably between 10 MHz and 250 MHz, depending on the liquid to be atomized, and this defines the electrode finger width and the gaps between them in the EWC-SPUDT.

The wick of the liquid delivery arrangement may be provided by at least one paper strip or string, with the liquid being delivered through capillary action. Other types of porous material providing a similar capillary action are also envisaged, for example cloth fabric, or other hydrophilic materials.

The liquid delivery arrangement may preferably also include a liquid reservoir container for containing the liquid to be delivered to the apparatus. The wick may extend from the surface of the piezoelectric substrate all the way to the interior of the liquid reservoir. Alternatively, a capillary tube may extend from the liquid reservoir, the wick receiving the liquid via this capillary tube. The liquid reservoir itself may be provided by a replaceable vial.

The capillary tube may preferably be of various shapes (bent to accommodate device design, for example), and placed with wick in a variety of orientations to contact the substrate and form the droplet. The capillary tube may however be omitted, with only the wick between the liquid reservoir and substrate.

A driver circuit preferably controls the apparatus based on the measurement of the user's breathing and safety interlocks on the apparatus as commanded through the user interface.

The use of surface acoustic wave (SAW) atomisation has a number of advantages over ultrasonic nebulization. Surface acoustic waves are MHz to GHz-order, transverse-axial polarized elliptical electroacoustic waves with displacement amplitudes of just a few nanometers. Here, they are generated on and traverse the surface of the piezoelectric substrate. Unlike typical ultrasound, which is a bulk phenomenon, the SAW is confined close to the substrate surface, its amplitude decaying rapidly over a depth of four to five wavelengths (several hundred microns) into the substrate material. Compared to conventional ultrasonic atomizers that consume power on the order of 10 W, the apparatus according to the present invention may only consume between 0.5-3 W since most of the energy is contained within a localized region close to the surface of the substrate and hence can be transmitted into the liquid much more efficiently than ultrasound. Moreover, the apparatus and power supply may be small showing the potential of the apparatus for portable applications. Moreover the 10-500 MHz order frequency employed in the apparatus is significantly higher than the 20 kHz-3 MHz frequency range of typical ultrasonic devices, induce vibrations with a period much shorter than the molecular relaxation time scale associated with large molecules in liquids, and thus the risk of denaturing molecules or lysing cells is greatly reduced. Further, as the frequency is increased, the power required to induce cavitation increases far beyond what is needed for atomisation, eliminating the effect of cavitation-induced lysis or shear in the apparatus.

In preliminary experiments conducted by the inventors on the atomization characteristics of a salbutamol ethanol/octanal solution, a mean aerosol diameter of 2.84±0.14 µm was achieved using SAW atomization. Salbutamol is a drug used in the treatment for asthma, and the aerosol diameters achieved are well within the optimal range for deep lung deposition.

Though the amplitude of a SAW is only a few nanometers, the acceleration of the surface is incredibly high ($10^7$ m$^2$/s) because of the high operating frequency. Therefore, when a SAW is transmitted into a liquid drop placed upon the substrate, it is able to not only form capillary waves across the free surface of the droplet but also drives it to break up into a mist of droplets with an average, controlled diameter of 1-10 µm. Micro and nanoparticles may be formed via controlled evaporation of these droplets, but irrespective of the desired product the challenge is in maintaining a relatively stationary free liquid surface on the SAW apparatus as an atomisation source.

The liquid delivery arrangement according to the present invention resolves these issues. Using a wick to siphon liquid from a liquid reservoir to the working surface of the apparatus provides it with continuous flow without pumping. The wick therefore permits atomisation without affecting the performance of the apparatus and offers a constraint sufficient to retain a stable meniscus outside the peripheral edge of the wick on the surface as noted in recent experiments by the inventors using such a paper wick. In these experiments, it was found that the meniscus is constantly replenished by liquid passing from the paper wick by liquid passing from the paper and provides a surface for the formation and destabilization of a capillary wave to eject the aerosol. The aerosol is ejected at an angle dependent upon the shape of the meniscus, itself dependent upon the power used to generate the SAW. The fluid absorption rate of the paper defines the upper limit in flow rate for the apparatus.

BRIEF DESCRIPTION OF THE DRAWINGS

It will be convenient to further describe the invention with respect to the accompanying drawings which illustrates a preferred embodiment of the apparatus according to the present invention. Other embodiments of the invention are possible, and consequently, the particularity of the accompanying drawings is not to be understood as superseding the generality of the preceding description of the invention.

In the drawings:

As shown in FIG. 1, the apparatus 1 according to the present invention includes a transducer element 3 having a piezoelectric substrate 5 providing a working surface 7 for the apparatus.

Figure 1:
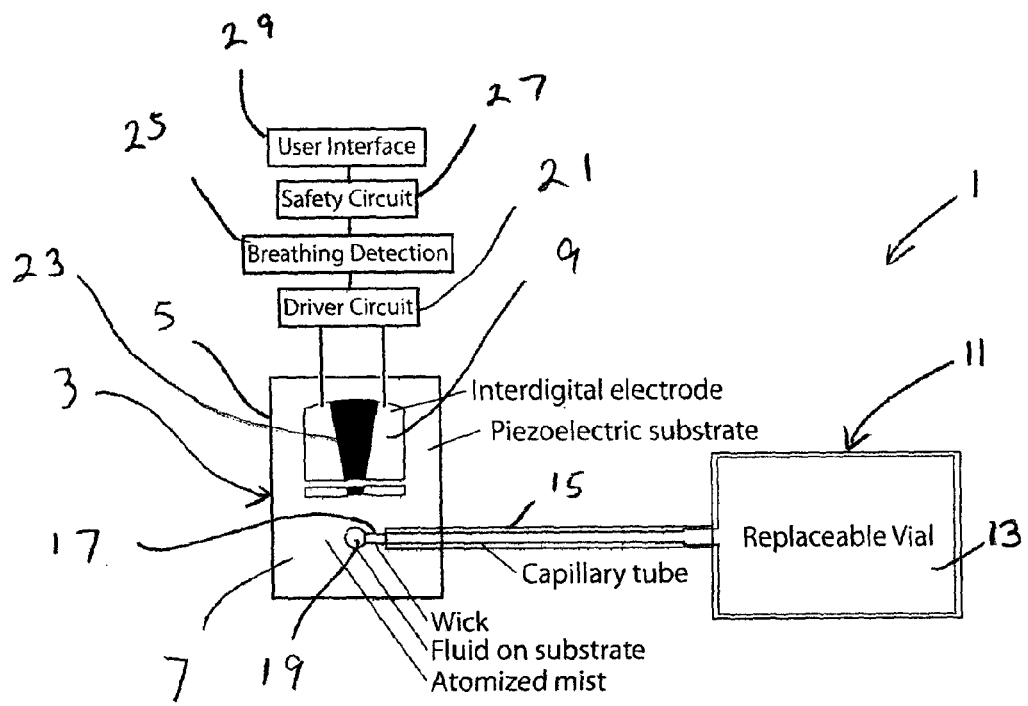
FIG. 1 is a schematic view of an apparatus for the atomization of a liquid according to the present invention.
Figure 2:
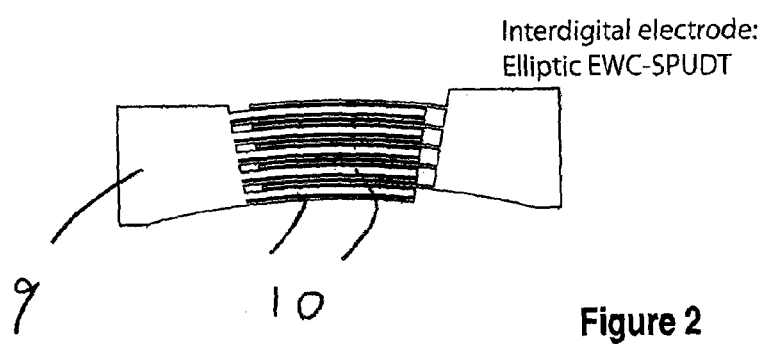
FIG. 2 is a schematic plan view of an interdigital electrode for the apparatus of FIG. 1.

Supported on the working surface 7 is an interdigital electrode 9 it has been found that the preferred electrode configuration is an elliptical electrode with controlled signal phase unidirectional transducer (EWC-SPUDT). It has been found that such an electrode provides the largest SAW intensity to the liquid delivered to the working surface 7. The interdigital electrode 9 is better shown in FIG. 2 which shows the electrode having a series of interlaced elliptically curved electrode fingers 10. The width and gap of these fingers may preferably be set to be a quarter of the SAW wavelength.

A liquid delivery arrangement 11 is provided for delivering liquid to the working surface 7. This arrangement includes a liquid reservoir 13 which may be in the form of a replaceable vial. A capillary tube 15 extends from the liquid reservoir 11 for supplying liquid to a wick 17 having one end thereof in contact with the working surface, the opposing end thereof being located within the capillary tube 15. The liquid delivery arrangement therefore enables a liquid meniscus 19 to be formed on the working surface 7 for atomisation.

The wick 17 can be in the form of a strip or string of paper, with one end of the wick being in contact with the working surface 7. As liquid is supplied to the working surface 7 through the wick 17, the meniscus 19 is formed between the end of the wick 17 and the working surface 7. This meniscus 19 is continuously replenished by liquid passing from the wick 17 and provides a surface for the formation and destabilisation of a capillary wave to eject the atomised droplets therefrom.

A driver circuit 21 applies an ultrasonic signal to the interdigital electrode 9, typically between 10 to 250 MHz, thereby resulting in a SAW 23 being generated in the working surface 7. The interaction of the SAW 23 with the liquid meniscus 19 results in an atomised mist of droplets.

The driver circuit 21 is controlled based on measurements of the user's breathing by a detection sensor 25, and by safety interlocks in a safety circuit 27 control through a user interface 29.

The apparatus 1 of the present invention has various applications and could be used for inhalation gene therapy and vaccination using genetic biomolecular materials, which could include plasmid DNA, siRNA, protein molecules, etc. Other applications may include DNA encapsulation, DNA stretching/hybridization and DNA micro-array printing.

It has also been found that the present invention advantageously reduces the risk of denaturing molecules since the period to induce vibrations in the apparatus 1 by employing 10-100 MHz order frequency is much shorter than the molecular relaxation time scale of macromolecules in liquids. In addition, cavitation is largely absent when the frequency is increased beyond a few MHz thus eliminating the effect of cavitation-induced lysis or shear for shear-sensitive molecules such as naked pDNA encoded with desired genes. Further, the size of droplets generated by the apparatus 1 can be changed by about an order of magnitude in a few microseconds in a controllable fashion by switching from a standing-wave to travelling-wave. Hence, the present invention has significant advantages over ultrasonic medical nebulizers that represent the current state of the art.

Further, SAW microfluidic actuation retains the benefits of using acoustic fields for driving fluid motion, namely, the large actuation speeds and the associated flow nonlinearities due to inertial forcing, while addressing the limitations that plague conventional ultrasonic methods. The high megahertz (>10 MHz) order SAW vibrations facilitate fluid and particle manipulation at a much finer scale, and provide more energy efficient mechanism by concentrating the energy into the narrow surface region of fluid. These exceptional advantages avoid the damage of DNA since the shear gradient generated within such a short period of time is not sufficient to degrade the DNA.

The SAW atomisation provided by the present invention is a viable means for generating aerosols of shear-sensitive biotherapeutics—plasmid DNA, and provides almost negligible denaturation of the supercoiled content. The present invention can be utilised to provide plasmid-laden aerosols which have a droplet size <5 μm for optimal deep lung deposition and remain biological active with tests demonstrating successful gene expression in mammalian cells after SAW atomisation. The apparatus 1 of the present invention is therefore suitable as a pulmonary delivery platform for DNA molecules, proteins and other biomolecules. Tests have also found that there is little damage to the mesenchymal stem cells, without hampering their viability, proliferation and differentiation after SAW irradiation. The low power requirement (as low as 1 W) compared with that required with conventional ultrasonic nebulizers allows the apparatus 1 to be miniaturised in a portable palm sized device, powered by battery and incorporated with advanced electronic detection and control for adaptive delivery.

The present invention provides an efficient and rapid process to generate biomolecule-laden aerosols with minimum disruption upon the innate structure of biomolecules, for example DNA biomolecules for gene therapy. This can advantageously minimise the waste of expensive molecules such as vaccines and drugs, and enable effective therapy as compared to all other atomisation processes which will destroy the biomolecules. The present invention provides a major breakthrough for aerosol gene delivery and provides great promise for non-viral gene therapy using a non-invasive approach.

Modifications and variations as would be deemed obvious to the person skilled in the art are included within the ambit of the present invention as claimed in the appended claims.

The invention claimed is:
1. An apparatus for the atomisation of a liquid including:
 a piezoelectric substrate having at least one working surface and at least one electrode supported on the piezoelectric substrate, the electrode being an elliptical electrode width controlled single phase unidirectional transducer (EWC SPUDT);

signal generating means for applying an ultrasonic signal to said electrode for generating a surface acoustic wave (SAW) in the working surface of the piezoelectric substrate; and a liquid delivery arrangement including a wick in contact with the working surface for delivering liquid thereof, wherein liquid delivered to the working surface is atomised by SAW irradiation.

2. An apparatus according to claim 1, wherein the wick of the liquid delivery arrangement is provided by at least one paper strip or string.

3. An apparatus according to claim 2, wherein the liquid delivery arrangement further includes a liquid reservoir for containing the liquid to be delivered to the apparatus.

4. An apparatus according to claim 3, further including a capillary tube extending from the liquid reservoir, the wick receiving the liquid via the capillary tube.

5. A method including the step of using the apparatus as claimed in claim 1 for pulmonary delivery of a nucleic acid composition.

6. A method including the step of using the apparatus as claimed in claim 1 for pulmonary delivery of salbutamol.

7. An apparatus for the atomization of a liquid including:

a piezoelectric substrate having at least one working surface upon which a drop of the liquid can be applied, at least one electrode supported on the piezoelectric substrate, the electrode being an elliptical electrode width controlled single phase unidirectional transducer (EWC SPUDT) and having an exit aperture, the ratio of the diameter of the liquid drop to exit aperture being between 0.5 and 2;

a signal generating means for applying an ultrasonic signal to said electrode for generating a surface acoustic wave (SAW) in the working surface of the piezoelectric substrate; and a liquid delivery arrangement including a wick in contact with the working surface for delivering liquid thereof, wherein liquid delivered to the working surface is atomized by SAW irradiation.

\* \* \* \* \*